United States Patent
Kogiso

(10) Patent No.: US 10,043,416 B2
(45) Date of Patent: Aug. 7, 2018

(54) MODEL FOR ENDOSCOPE

(71) Applicant: OLYMPUS CORPORATION, Hachioji-shi, Tokyo (JP)

(72) Inventor: Junichi Kogiso, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/202,942

(22) Filed: Jul. 6, 2016

(65) Prior Publication Data

US 2016/0314714 A1  Oct. 27, 2016

Related U.S. Application Data

(63) Continuation of application No. PCT/JP2015/065766, filed on Jun. 1, 2015.

(30) Foreign Application Priority Data

Jul. 3, 2014  (JP) .................................. 2014-137726

(51) Int. Cl.
*G09B 23/34* (2006.01)
*G09B 23/28* (2006.01)
(Continued)

(52) U.S. Cl.
CPC ........ *G09B 23/285* (2013.01); *A61B 1/00057* (2013.01); *G09B 23/306* (2013.01)

(58) Field of Classification Search
CPC ...... G09B 23/28; G09B 23/285; G09B 23/30; G09B 23/306; A61B 1/00
(Continued)

(56) References Cited

U.S. PATENT DOCUMENTS 2,017,250 A * 10/1935 Jones .................. C14B 1/26
 105/409
4,386,917 A * 6/1983 Forrest .................. G09B 23/28
 434/267
(Continued)

FOREIGN PATENT DOCUMENTS

JP  2004-049479 A  2/2004
JP  2004-347623 A  12/2004
(Continued)

OTHER PUBLICATIONS

Aug. 25, 2015 International Search Report issued in Patent Application No. PCT/JP2015/065766.
(Continued)

*Primary Examiner* — Sam Yao
*Assistant Examiner* — Jennifer L Korb
(74) *Attorney, Agent, or Firm* — Oliff PLC

(57) ABSTRACT

A model for an endoscope includes a tissue holding portion including: a first member which has a through hole, which is hard, and which is formed in a frame shape; and a second member which is formed in a sheet shape with a material that is more flexible than the first member and is elastically deformable, which has a window portion that penetrates the second member in a thickness direction of the second member, and which is attached to the first member. A piece of tissue is attached to the second member such that the piece of tissue overlaps the window portion, and the second member is attached to the first member in a state in which the second member is elastically deformed so that tension acts on the second member.

7 Claims, 3 Drawing Sheets

(51) Int. Cl.
*G09B 23/30* (2006.01)
*A61B 1/00* (2006.01)

(58) Field of Classification Search
USPC .................................. 434/262, 267, 272
See application file for complete search history.

(56) References Cited

U.S. PATENT DOCUMENTS

| | | | | |
|---|---|---|---|---|
| 5,358,408 | A * | 10/1994 | Medina | G09B 23/28 |
| | | | | 434/262 |
| 8,465,771 | B2 * | 6/2013 | Wan | F16L 9/00 |
| | | | | 424/477 |
| 9,548,002 | B2 * | 1/2017 | Black | G09B 23/285 |
| 2002/0191406 | A1 * | 12/2002 | Hashitani | G01R 1/06755 |
| | | | | 362/458 |
| 2007/0020598 | A1 | 1/2007 | Yamashita et al. | |
| 2012/0029416 | A1 * | 2/2012 | Parker | A61F 13/02 |
| | | | | 604/20 |
| 2014/0087347 | A1 | 3/2014 | Tracy et al. | |

FOREIGN PATENT DOCUMENTS

| | | | |
|---|---|---|---|
| JP | 2006-116206 A | | 5/2006 |
| JP | 2006116206 A | * | 5/2006 |
| JP | 2008-197483 A | | 8/2008 |
| WO | 2007/068360 A1 | | 6/2007 |

OTHER PUBLICATIONS

Nov. 6, 2017 Search Report issued in European Patent Application No. 15814914.6.

\* cited by examiner

MODEL FOR ENDOSCOPE

This application is a continuation application based on PCT Patent Application No. PCT/JP2015/065766, filed Jun. 1, 2015, whose priority is claimed on Japanese Patent Application No. 2014-137726, filed Jul. 3, 2014. The contents of both the PCT Patent Application and the Japanese Patent Application are incorporated herein by reference.

BACKGROUND OF THE INVENTION

Field of the Invention

The present invention relates to a model for an endoscope (a human body model). More particularly, the present invention relates to a model for an endoscope (a human body model) used for training in operation of a flexible endoscope or the like and performance evaluation of the flexible endoscope or the like.

Description of Related Art

Conventionally, in training in operation of a flexible endoscope or the like and performance evaluation of a flexible endoscope or the like, models for endoscopes formed to simulate human organs have been used. Such models for endoscopes are also used for training in various endoscopic operations. However, since it is necessary to use actual organ tissue in training in procedures such as endoscopic mucosal dissection or suturing, at least a part for performing the procedure is more commonly formed, using slices of visceral tissue such as that of pigs and cows.

Japanese Unexamined Patent Application, First Publication No. 2006-116206 discloses an endoscopic incision and dissection model that includes a simulated organ having the shape of a predetermined organ and a frame-shaped member capable of fixing the mucosal tissue. The frame-shaped member is incorporated in a window provided in the simulated organ.

SUMMARY OF THE INVENTION

According to a first aspect of the present invention, a model for an endoscope includes: a first member; and a second member having a fixing portion to which the first member is fixed, the second member being configured to hold a piece of tissue at a position spaced apart from the fixing portion, the second member having a section that is more flexible than the first member and is elastically deformable.

According to a second aspect of the present invention, in the model according to the first aspect, the first member may be a frame that constitutes an edge of a through hole. The second member may be formed in a sheet shape, the second member may have a window portion that penetrates the second member in a thickness direction of the second member, the second member may hold the piece of tissue such that the piece of tissue is exposed at an inner side of an edge of the window portion, and the second member may be fixed to the first member such that the through hole and the window portion communicate with each other.

According to a third aspect of the present invention, in the model according to the second aspect, the second member may be attached to the first member in a state in which the second member is elastically deformed so that tension acts on the second member.

According to a fourth aspect of the present invention, in the model according to the third aspect, the second member may be configured to have anisotropic flexibility.

According to a fifth aspect of the present invention, in the model according to the third aspect, the second member may be attached to the first member such that the window portion is entirely located at an inner side of the through hole.

DETAILED DESCRIPTION OF THE INVENTION

First Embodiment

Figure 1:
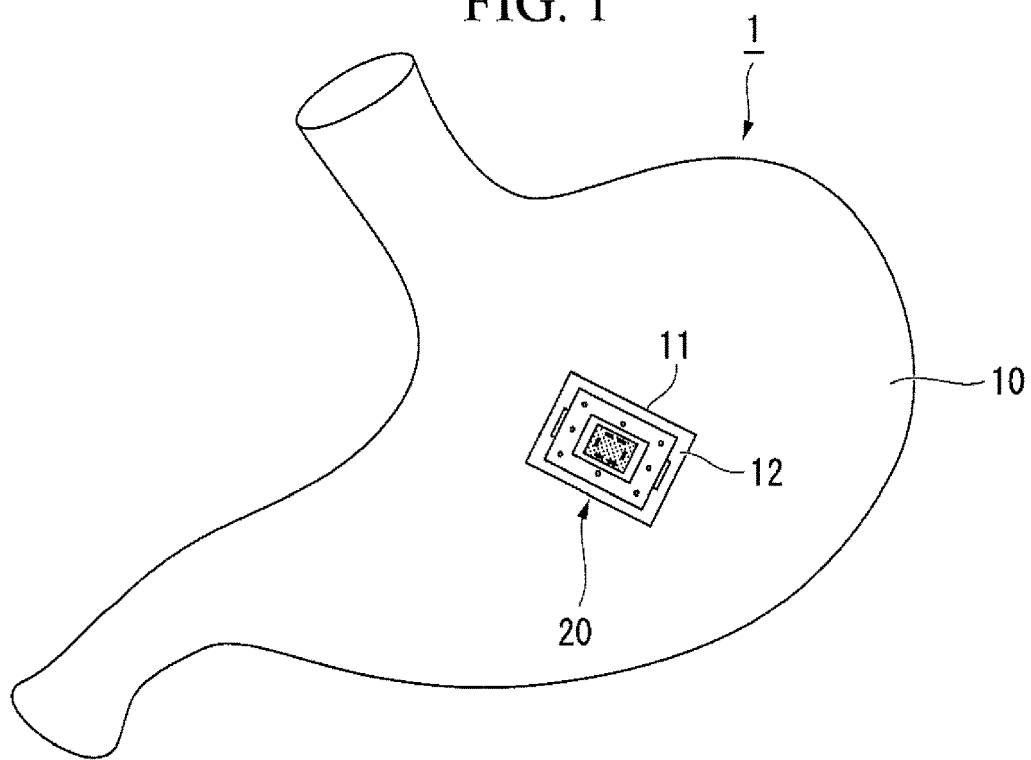
FIG. 1 is a diagram showing a model for an endoscope according to a first embodiment of the present invention.

A first embodiment of the present invention will be described with reference to FIGS. 1 to 4. FIG. 1 is a diagram showing a model 1 for an endoscope according to the present embodiment. The model 1 for an endoscope is a model simulating a human stomach. The model 1 for an endoscope includes a basic shape portion 10 formed to simulate a stomach, and a tissue holding portion 20 that is detachably attached to the basic shape portion 10.

The basic shape portion 10 is formed by appropriately setting its shape and material, depending on tubular organs or tubular parts serving as a target of training and performance evaluation (hereinafter referred to as "training or the like") of an endoscope and a treatment tool for the endoscope. A mounting hole 11 communicating with the interior space is provided at the basic shape portion 10. A hard fixing frame 12 to which the tissue holding portion 20 is detachably attached is mounted on the circumferential edge portion of the mounting hole 11. The shape of the fixing frame 12 is formed to correspond to the shape of the tissue holding portion 20.

Figure 2:
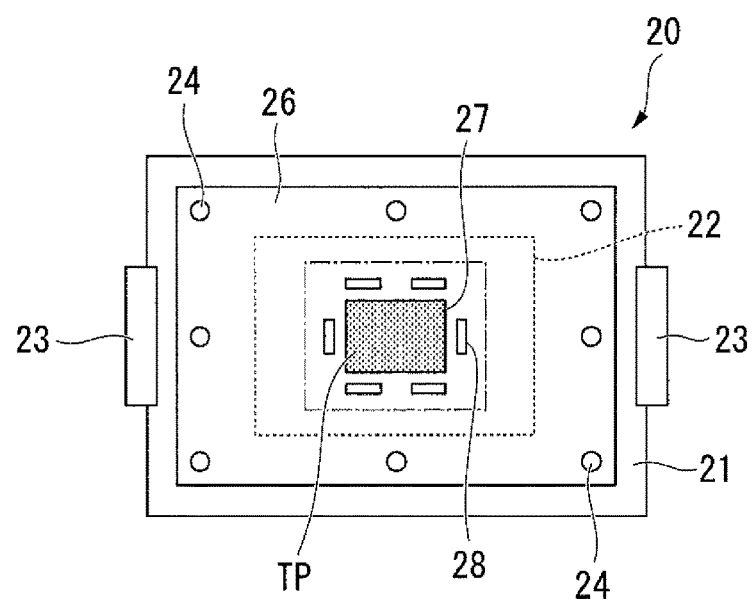
FIG. 2 is a bottom view of a tissue holding portion.
Figure 3:
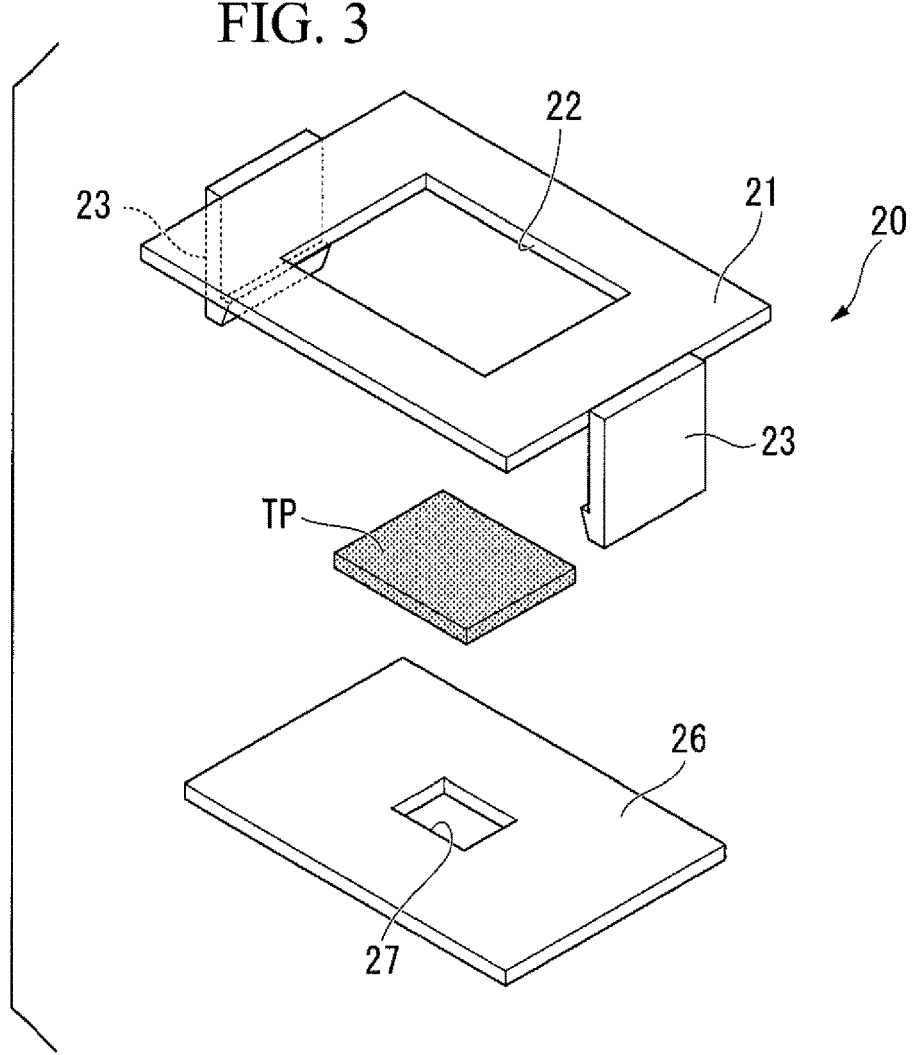
FIG. 3 is an exploded view showing the tissue holding portion of the model for an endoscope.
Figure 4:
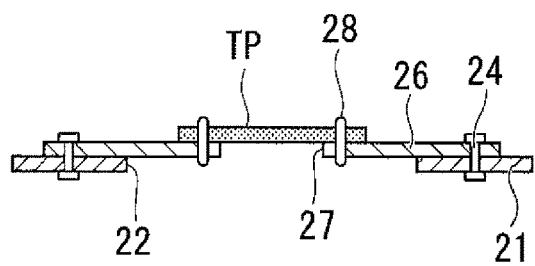
FIG. 4 is a cross-sectional view of a tissue holding portion in a modified example.

FIG. 2 is a bottom view of the tissue holding portion 20. FIG. 3 is an exploded view showing the tissue holding portion 20. The tissue holding portion 20 includes a hard first member 21 detachably attached to the fixing frame 12, and a second member 26 which is formed of a material more flexible than the first member 21 and is mounted to the first member 21.

The first member 21 is formed of a material having relatively high rigidity, such as metal or resin. The first member 21 is formed in a frame shape by forming a rectangular through hole 22 in the central portion. Claw portions 23 for being engaged with the fixing frame are provided on the circumferential edges of the first member 21. The presence or absence of the claw portions 23, the number of the claw portions 23 that are provided, and the shapes and the positions thereof can be appropriately set.

The second member 26 is formed of a material more flexible than the first member 21, for example, rubber or silicone, in a sheet shape, and can be elastically deformed by applying a force in a surface direction. By forming the second member 26 such that a rectangular window portion 27 penetrates the central portion of the second member 26 in the thickness direction, the second member 26 is formed in a frame shape similar to the first member 21. As shown in FIG. 3, an area of the window portion 27 is smaller than an area of the through hole 22. It is possible to dispose the first member 21 and the second member 26 such that they overlap each other so that the whole window portion 27 is located in the through hole 22.

A piece of tissue TP is formed in a shape and a size capable of covering the window portion 27. The piece of tissue TP is disposed to cover the whole window portion 27 and is fixed to the second member 26 by a linear member 28. As the linear member 28, it is possible to use a medical suture, a sewing thread, a resin gut, or the like.

The first member 21 and the second member 26 are fixed on the outside of the through hole 22 and the window portion 27 by a plurality of pins 24. The second member 26 is fixed to the first member 21 in a state in which the second member 26 is stretched in the surface direction and elastically deformed. Thus, tension of magnitude corresponding to the elastic deformation acts on the second member 26 and the piece of tissue TP fixed to the second member 26.

When forming the tissue holding portion 20 to which the piece of tissue TP is fixed, first, the piece of tissue TP is fixed to the second member 26 by the linear member 28 to overlap the window portion 27. Thereafter, the second member 26 is fixed to the first member 21 in a state in which tension acts on the second member 26. For example, first, parts of the circumferential edge portion of the second member 26 are fixed to the first member 21 by the pins 24, and the non-fixed parts of the circumferential edge portion are stretched and elastically deformed to be spaced apart from the fixed parts. Thereafter, the remaining parts of the circumferential edge portion are fixed to the first member 21, while the elastically deformed state is maintained.

When the piece of tissue TP is attached to the tissue holding portion 20, the claw portions 23 of the first member 21 are engaged with the fixing frame 12 while causing the second member 26 to face the basic shape portion 10, and the tissue holding portion 20 is attached to the basic shape portion 10. Thus, the model 1 for an endoscope becomes usable.

A user can perform training or the like in the desired contents by inserting an endoscope (not shown) into the basic shape portion 10 to move the tip of the endoscope to the vicinity of the window portion 27, or by performing procedures on a part of the piece of tissue TP exposed from the window portion 27 using a treatment tool (not shown) inserted into the endoscope. When training or the like concerning a procedure is performed, a plurality of tissue holding portions 20 with pieces of tissue fixed thereto are prepared in advance and the tissue holding portions 20 are sequentially replaced after the procedure is performed, and thus training or the like can be continuously performed. When training or the like is performed using an energized treatment tool such as a high-frequency knife, a counter electrode member having conductivity is attached to an end portion of the piece of tissue TP, or the counter electrode member attached to the distant position and the piece of tissue TP are connected to a gauze soaked in saline, and thus the power supply can be applied to the piece of tissue TP.

Tension caused by the elastic force of the second member 26 acts on the piece of tissue TP exposed through the window portion 27. Thus, for example, when training or the like is performed on the piece of tissue TP, it is possible to reproduce conditions similar to those of a procedure actually performed on a living body with regard to the behavior and feeling of the tissue and it is possible to effectively perform training or the like.

As described above, according to the model 1 for an endoscope of the present embodiment, in the tissue holding portion 20 on which the piece of tissue TP is held, the piece of tissue TP is fixed to the first member 21 via the second member 26 that is more flexible than the first member, rather than being directly fixed to the hard first member 21. Accordingly, even when the size of the piece of tissue TP is reduced for uniformity of the tissue when a plurality of pieces of tissue are prepared, the distance between the tissue exposed from the window portion and the part fixed to the first member 21 can be sufficiently secured by the second member 26. As a result, it is possible to reduce the influence of the first member 21 on the tension acting on the piece of tissue TP, and to approximate the behavior and feeling of the tissue to those of actual tissue.

Further, in general, since the surface of the piece of tissue is very slippery, it is difficult to fix the piece of tissue to the first member in a state in which the tension acts on the piece of tissue. However, when the piece of tissue is fixed via the second member 26, even if the piece of tissue is fixed to the second member 26 in a state in which the tension does not act on the piece of tissue, by fixing the piece of tissue to the first member 21 by causing the tension to act on the second member 26 thereafter, it is possible to allow the tension to easily act on the piece of tissue TP. Therefore, it is possible to very easily perform the work of fixing the piece of tissue TP to the tissue holding portion 20 in a state in which the tension acts on the piece of tissue TP, and even when a plurality of tissue holding portions are prepared in advance, the tissue holding portions can be efficiently prepared.

Further, when the second member 26 is attached to the first member 21, the edge of the opening of the window portion 27 extends to the inner side from the edge of the opening of the through hole 22 over the entire circumference, and is located on the inner side from the edge of the opening of the through hole 22 of the first member 21. That is, the opening area of the window portion 27 is smaller than the opening area of the through hole 22. In this case, the tissue fixed to the window portion 27 can be connected to the first member 21 via the second member 26 over the entire circumference. As a result, it is possible to approximate the tension acting on the piece of tissue TP to natural tension (tension acting on tissue of an actual patient).

In the present embodiment, although an example in which the piece of tissue is disposed between the first member and the second member in the thickness direction of the tissue holding portion has been described, the arrangement is not limited thereto. For example, as in a modified example shown in FIG. 4, the second member 26 may be disposed between the piece of tissue TP and the first member 21. Further, even when the piece of tissue is disposed between the first member and the second member, as long as the piece of tissue is not directly fixed to the first member, a part of the piece of tissue may be disposed to be interposed between the first member and the second member.

Further, the fixing manner of the piece of tissue and the second member, and the fixing manner of the second member and the first member are not limited to the aforementioned examples, and may be used by appropriately selecting various known fixing means.

Second Embodiment

Next, a second embodiment of the present invention will be described with reference to FIG. 5. The present embodiment differs from the first embodiment in the structure of the second member. In addition, in the following description, the configurations common to those described above will be denoted by the same reference numerals and a repeated description will not be provided.

Figure 5:
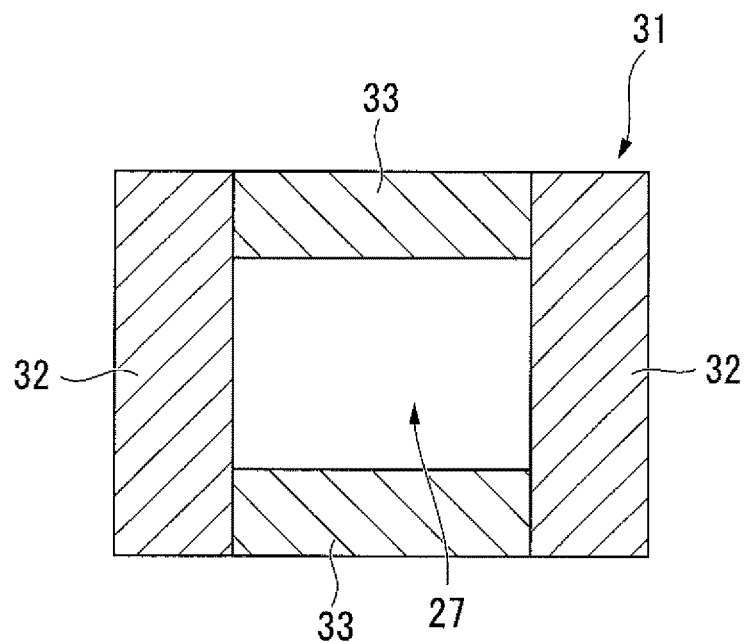
FIG. 5 is a diagram showing a second member in a model for an endoscope according to a second embodiment of the present invention.

FIG. 5 is a plan view showing a second member 31 in a tissue holding portion according to a model for an endoscope of the present embodiment. The second member 31 is configured using a first material 32 that is more flexible than the first member 21, and a second material 33 that is more flexible than the first material 32.

Both of the first material 32 and the second material 33 are formed in a sheet shape having a rectangular shape in a plan view. As shown in FIG. 5, two pieces of the first material 32 are disposed on both sides in the longitudinal direction of the rectangular window portion 27, and two pieces of the second material 33 are disposed on both sides in the width direction (lateral direction) of the window portion 27. The first material 32 and the second material 33 are connected to each other in this arrangement, and thus the second member 31 of the present embodiment is formed. The second member 31 is more easily stretched in the longitudinal direction of the window portion 27 due to the aforementioned structure, thus providing anisotropic flexibility.

In the model for an endoscope of the present embodiment, similarly to the first embodiment, it is also possible to achieve both uniformity of the tissue and reproduction of the condition similar to that of a procedure actually performed in a living body. Further, since the second member 31 is configured to have anisotropic flexibility, when the orientation is appropriately set at the time of fixing to the first member in consideration of the aforementioned anisotropy, the behavior and feeling of the tissue can further approximate those of the desired tubular organ. As a result, it is possible to further enhance the quality of training or the like.

Although an example in which the second member is formed using two types of materials with different flexibility has been described in the present embodiment, a method of providing anisotropic flexibility of the second member is not limited thereto. Accordingly, the second member may be formed using three or more kinds of materials with different flexibility, or the second member may be formed using a single material that already has anisotropic flexibility.

Although the model for an endoscope of the present invention has been described using the embodiments, the technical scope of the present invention is not limited to the aforementioned embodiments, and it is possible to change the combinations of the constituent elements or to add various changes to the constituent elements or delete them without departing from the spirit and scope of the present invention.

For example, in the present invention, the basic shape portion may be flexibly formed. However, in this case, at least the fixing frame is formed of a hard material so that tension can be appropriately provided to the piece of tissue.

Figure 6:
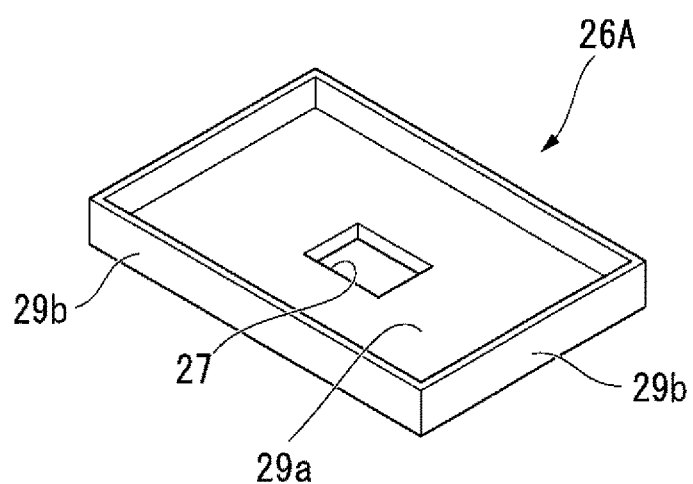
FIG. 6 is a perspective view showing a second member in a modified example of a model for an endoscope of the present invention.

Moreover, the first member may be provided in the basic shape portion without being provided in the tissue holding portion. For example, the aforementioned fixing frame 12 is provided as the first member, and as in the second member 26A of the modified example shown in FIG. 6, the second member is formed to have a planar portion 29a having a window portion 27, and a fitting portion 29b which rises from the circumferential edges of the planar portion 29a with respect to the planar portion 29a at an angle. As long as the piece of tissue is fixed to the second member 26A and the fitting portion 29b is fitted at the outside of the fixing frame 12 and attached to the fixing frame 12 in a state in which the planar portion 29a is stretched, it is possible to allow tension to act on the second member and the piece of tissue fixed to the second member.

Further, the shapes of the through hole and the window portion, and the external shapes in the plan view of the first member and the second member may not be rectangular and may be appropriately set.

Further, in the model for an endoscope of the present invention, the piece of tissue may not necessarily be attached to the second member to completely cover the window portion, and at least a part of the piece of tissue may be disposed to overlap the window portion.

In addition, the basic shape portion is not essential in the model for an endoscope of the present invention. Thus, it is also possible to use only the aforementioned tissue holding portion 20 depending on the content of training or the like.

Further, in the model for an endoscope of the present invention, the basic shape portion is not limited to the model of the human stomach. As long as the basic shape portion is a model (a human body model) that simulates a human digestive tract (large intestine, esophagus, or the like), similar training effects can be obtained.

The present invention is not limited by the aforementioned description, and is only limited by the scope of the appended claims.

What is claimed is:

1. A model for an endoscope comprising:
a first member being a frame that forms an edge of a through hole; and
a second member including:
a fixing portion to which the first member is fixed, the second member being configured to hold a piece of tissue at a position spaced apart from the fixing portion; and
a section that is more flexible than the first member and is elastically deformable, wherein:
the second member is formed in a sheet shape,
the second member has a window portion that penetrates the second member in a thickness direction of the second member,
the second member is configured to hold the piece of tissue such that the piece of tissue is exposed at an inner side of an edge of the window portion,
the second member is fixed to the first member such that the through hole and the window portion communicate with each other, and
the second member is stretched to be elastically deformed and attached to the first member by applying a force in an in-plane direction such that a tension acts on the second member, the tension acting on the second member generating another tension acting on an entirety of the piece of tissue to stretch the piece of tissue and fix the piece of tissue in accordance with the tension acting on the second member.

2. The model according to claim 1, wherein the second member is configured to have anisotropic flexibility.

3. The model according to claim 1, wherein the second member is attached to the first member such that the window portion is entirely located at an inner side of the through hole.

4. The model according to claim 1, further comprising a claw portion configured to engage the first member with a fixing frame.

5. The model according to claim 1, wherein
the through hole penetrates a central portion of the first member in a thickness direction of the first member, and the window portion is disposed at a central portion of the second member.

6. The model according to claim 1, wherein the window portion of the second member has a same shape as the through hole of the first member.

7. The model according to claim 1, wherein the edge of the through hole of the first member is parallel to an edge of the window portion of the second member.

* * * * *